(12) United States Patent
Grata et al.

(10) Patent No.: US 9,037,206 B2
(45) Date of Patent: May 19, 2015

(54) METHOD AND APPARATUS FOR THE NON-INVASIVE SENSING OF GLUCOSE IN A HUMAN SUBJECT

(75) Inventors: Jeremy Grata, Indiana, PA (US); Michael N. Pitsakis, Amherst, NY (US)

(73) Assignee: Dominion Assets, LLC, Potomac Falls, VA (US)

( * ) Notice: Subject to any disclaimer, the term of this patent is extended or adjusted under 35 U.S.C. 154(b) by 0 days.

(21) Appl. No.: 13/423,705

(22) Filed: Mar. 19, 2012

(65) Prior Publication Data

US 2012/0238844 A1 Sep. 20, 2012

Related U.S. Application Data

(60) Division of application No. 11/599,190, filed on Nov. 14, 2006, now Pat. No. 8,140,139, and a continuation-in-part of application No. 11/451,864, filed on Jun. 13, 2006, now abandoned.

(60) Provisional application No. 60/690,418, filed on Jun. 14, 2005.

(51) Int. Cl.
*A61B 5/1455* (2006.01)
*A61B 5/11* (2006.01)
(Continued)

(52) U.S. Cl.
CPC ........... *A61B 5/1112* (2013.01); *A61B 5/14532* (2013.01); *A61B 5/14546* (2013.01);
(Continued)

(58) Field of Classification Search
USPC ................................................. 600/309–344
See application file for complete search history.

(56) References Cited

U.S. PATENT DOCUMENTS

| | | | |
|---|---|---|---|
| 4,655,225 | A | 4/1987 | Dahne et al. |
| 5,070,874 | A | 12/1991 | Barnes et al. |

(Continued)

FOREIGN PATENT DOCUMENTS

| | | |
|---|---|---|
| CN | 1214768 A | 4/1999 |
| EP | 0692222 A1 | 1/1996 |

(Continued)

OTHER PUBLICATIONS

Marbach R. "On Wiener filtering and the physics behind statistical modeling" Journal of Biomedical Optics, vol. 7, No. 1, Jan. 2002, pp. 130-147.

(Continued)

*Primary Examiner* — Eric Winakur
*Assistant Examiner* — Marjan Fardanesh
(74) *Attorney, Agent, or Firm* — The Webb Law Firm (57) ABSTRACT

An apparatus for a non-invasive sensing of biological analytes in a sample includes an optics system having at least one radiation source and at least one radiation detector; a measurement system operatively coupled to the optics system; a control/processing system operatively coupled to the measurement system and having an embedded software system; a user interface/peripheral system operatively coupled to the control/processing system for providing user interaction with the control/processing system; and a power supply system operatively coupled to the measurement system, the control/processing system and the user interface system for providing power to each of the systems. The embedded software system of the control/processing system processes signals obtained from the measurement system to determine a concentration of the biological analytes in the sample.

11 Claims, 8 Drawing Sheets

(51) Int. Cl.
*A61B 5/145* (2006.01)
*G01J 1/46* (2006.01)
*G01J 3/02* (2006.01)
*G01J 3/42* (2006.01)
*G01N 21/359* (2014.01)

(52) U.S. Cl.
CPC ............... *A61B5/1455* (2013.01); *G01J 1/46* (2013.01); *G01J 3/02* (2013.01); *G01J 3/027* (2013.01); *G01J 3/42* (2013.01); *G01N 21/359* (2013.01); *A61B 2562/0233* (2013.01)

(56) References Cited

U.S. PATENT DOCUMENTS

| | | | |
|---|---|---|---|
| 5,077,476 A | 12/1991 | Rosenthal | |
| 5,086,229 A | 2/1992 | Rosenthal et al. | |
| 5,313,941 A * | 5/1994 | Braig et al. | 600/322 |
| 5,360,004 A | 11/1994 | Purdy et al. | |
| 5,379,764 A | 1/1995 | Barnes et al. | |
| 5,460,177 A | 10/1995 | Purdy et al. | |
| 5,471,981 A | 12/1995 | Wiggins et al. | |
| 5,533,509 A | 7/1996 | Koashi et al. | |
| 5,574,283 A | 11/1996 | Quintana | |
| 5,703,364 A | 12/1997 | Rosenthal | |
| 5,754,333 A | 5/1998 | Fulbert et al. | |
| 5,891,024 A * | 4/1999 | Jarman et al. | 600/323 |
| 5,892,586 A | 4/1999 | Thony et al. | |
| 5,919,133 A * | 7/1999 | Taylor et al. | 600/323 |
| 5,945,676 A | 8/1999 | Khalil et al. | |
| 6,016,435 A | 1/2000 | Maruo et al. | |
| 6,026,314 A | 2/2000 | Amerov et al. | |
| 6,034,367 A | 3/2000 | Waczynski et al. | |
| 6,040,578 A | 3/2000 | Malin et al. | |
| 6,061,582 A | 5/2000 | Small et al. | |
| 6,064,054 A | 5/2000 | Waczynski et al. | |
| 6,080,983 A | 6/2000 | Waczynski et al. | |
| 6,088,605 A | 7/2000 | Griffith et al. | |
| 6,097,975 A | 8/2000 | Petrovsky et al. | |
| 6,107,630 A | 8/2000 | Mazurowski et al. | |
| 6,172,743 B1 | 1/2001 | Kley et al. | |
| 6,219,565 B1 | 4/2001 | Cupp et al. | |
| 6,236,047 B1 | 5/2001 | Malin et al. | |
| 6,253,097 B1 | 6/2001 | Aronow et al. | |
| 6,280,381 B1 | 8/2001 | Malin et al. | |
| 6,309,884 B1 | 10/2001 | Cooper et al. | |
| 6,728,560 B2 | 4/2004 | Kollias et al. | |
| 6,775,564 B1 | 8/2004 | Peters et al. | |
| 6,816,241 B2 | 11/2004 | Grubisic | |
| 6,836,678 B2 | 12/2004 | Tu | |
| 6,850,790 B2 | 2/2005 | Berner et al. | |
| 2002/0016719 A1 | 2/2002 | Nemeth et al. | |
| 2002/0082487 A1 | 6/2002 | Kollias et al. | |
| 2003/0144582 A1 | 7/2003 | Cohen et al. | |
| 2004/0068163 A1 | 4/2004 | Ruchti et al. | |
| 2005/0010090 A1 | 1/2005 | Acosta et al. | |
| 2005/0020892 A1 | 1/2005 | Acosta et al. | |
| 2005/0030540 A1 | 2/2005 | Thorton | |
| 2005/0090723 A1 | 4/2005 | Saeed | |
| 2005/0250997 A1 | 11/2005 | Takeda et al. | |
| 2005/0256384 A1 | 11/2005 | Walker et al. | |
| 2005/0261560 A1 | 11/2005 | Ridder et al. | |

FOREIGN PATENT DOCUMENTS

| | | |
|---|---|---|
| EP | 0880936 A2 | 12/1998 |
| WO | 2004090510 A1 | 10/2004 |
| WO | 2005070291 A1 | 8/2005 |
| WO | 2006047388 A2 | 5/2006 |

OTHER PUBLICATIONS

Stephen F. Malin et al., Noninvasive Prediction of Glucose by Near-Infrared Diffuse Reflectance Spectroscopy; Oak Ridge Conference, Clinical Chemistry 45:9, 1651-1658 (1999).

* cited by examiner

METHOD AND APPARATUS FOR THE NON-INVASIVE SENSING OF GLUCOSE IN A HUMAN SUBJECT

CROSS REFERENCE TO RELATED APPLICATIONS

This application is a divisional of U.S. patent application Ser. No. 11/599,190, filed Nov. 14, 2006, now U.S. Pat. No. 8,140,139 which is a continuation-in-part of U.S. patent application Ser. No. 11/451,864, filed Jun. 13, 2006, and claims benefit of priority to Provisional Patent Application No. 60/690,418, filed Jun. 14, 2005, all entitled "Method and Apparatus for the Non-Invasive Sensing of Glucose in a Human Subject", which are hereby incorporated by reference in their entirety.

BACKGROUND OF THE INVENTION

1. Field of the Invention

The present invention relates, in general, to noninvasive sensing of biological analytes in the capillary vessels and in interstitial fluid. More specifically, the present invention relates to a method and an apparatus for the determination of blood glucose, lipids and/or alcohol concentration at regular short intervals on a continuous basis or on demand.

2. Description of Related Art

Diabetes is a group of diseases characterized by high levels of blood glucose resulting from defects in insulin production, insulin action, or both. The Diabetes Control and Complications Trial (DCCT), a ten year clinical study conducted between 1983 and 1993 by the National Institute of Diabetes and Digestive and Kidney Diseases, demonstrated a direct positive correlation between high average blood glucose levels, known as hyperglycemia and the development of devastating complications of the disease that affect the kidneys, eyes, nervous system, blood vessels and circulatory system. Treatment includes insulin injections, oral medication, diet control and exercise. Adjustment of the user's regimen by a physician to control hyperglycemia requires routine self-monitoring of glucose levels three or more times per day. Currently persons with diabetes measure their glucose levels by using invasive blood glucose instruments that measure glucose using expensive disposable test strips where a small sample of blood obtained from a finger or the forearm is applied. The procedure is very painful and often results in chronic nerve ending damage. This is one reason many diabetes patients forego monitoring risking the development of serious complications.

Many prior art systems utilize diffuse reflectance spectroscopy to determine blood glucose concentration in tissue. For instance, U.S. Pat. No. 6,097,975 to Petrovsky et al. discloses an apparatus and method for non-invasively measuring blood glucose concentration. The apparatus projects a beam of light (2050-2500 nm) to a selected area of the body that is rich in blood vessels, such as the inner wrist or ear lobes. The projected pulse of light is transmitted through the skin, tissues and blood vessels, partially absorbed by glucose in the blood and partially scattered, diffused and reflected off of irradiated structures back through the blood vessels, tissue and skin. The luminous energy of the reflected light is then collected by a receiving detector, converted to an electrical signal proportional to the glucose concentration in the blood of the subject and analyzed. The wavelength range of the preferred embodiment disclosed in this reference utilizes the wavelength range of 2050-2500 nm.

U.S. Pat. No. 6,016,435 to Maruo et al. discloses a device for non-invasive determination of a glucose concentration in the blood of a subject. The device includes a light source, a diffraction grating unit as a spectroscope of the light provided by the light source and a stepping motor unit for controlling a rotation angle of the diffraction grating to provide near-infrared radiation having successive wavelengths from 1300-2500 nm. The device further includes an optical fiber bundle having a plurality of optical fibers for projecting the near-infrared radiation onto the skin of a subject and a plurality of second optical fibers for receiving the resulting radiation emitted from the skin. A light receiving unit is connected to the second optical fibers and a spectrum analyzing unit determines the glucose concentration in the blood through the use of spectrum analysis based on information from the light receiving unit. This invention differs from the present invention in that it utilizes a continuous spectrum lamp and a diffraction grating with mechanically moving parts.

U.S. Pat. No. 5,533,509 to Koashi et al. discloses an apparatus for non-invasive measurement of blood sugar level. The apparatus includes a wavelength-variable semiconductor laser that tunes in small ranges around wavelengths of interest producing a beam that is separated into two optical paths with a beam splitter and an integrating sphere that collects laser light transmitted or reflected after passing along an optical path and made incident on an examined portion of skin in which the blood glucose level is determined by examining the derivative of the absorbance spectrum. The present invention differs from this reference in that the skin is probed over the entire range with a plurality of wavelengths and not just certain wavelengths, and the absorbance spectrum, not the derivative of the absorption spectrum, is used to determine glucose concentration.

United States Patent Application Publication No. 2005/0250997 to Takeda et al. discloses an apparatus for determining a concentration of a light absorbing substance in blood. The apparatus includes a plurality of photo emitters that emit light beams having different wavelengths toward a living tissue. A photo receiver is adapted to receive the light beams which have been transmitted through or reflected from the living tissue. However, the preferred embodiment of this invention calls for only two light emitting diodes; one at 680 nm and one at 940 nm.

United States Patent Application Publication No. 2005/0256384 to Walker et al. discloses a non-invasive glucose sensor including at least one laser (Vertical Cavity Surface Emitting Laser (VCSEL) or edge emitting) and at least one photo detector configured to detect emissions from the emitter. The glucose sensor further includes a controller driving one or more emitters by shifting emitter wavelength by 1-2 nm from a group of selected wavelengths having center wavelengths of 1060 nm, 980 nm, 850 nm, 825 nm, 800 nm, 780 nm and 765 nm. This enables measurement of absorption at a plurality of wavelengths and derivation of a glucose concentration measurement from the absorption measurement values. The wavelength range of operation of this apparatus is outside the wavelength range of the present invention.

U.S. Pat. No. 5,703,364 to Rosenthal discloses a method for performing near-infrared (NIR) quantitative analysis. The method includes the steps of providing NIR radiation at a plurality of different wavelengths (600-1100 nm) for illumination of an object to be analyzed and varying the amount of time that radiation at each wavelength illuminates the subject according to the output level of radiation at each wavelength so as to provide substantially similar detection data resolution for each of the plurality of wavelengths. The wavelength range of operation of this apparatus is outside the wavelength range of the present invention.

U.S. Pat. No. 6,816,241 to Grubisic discloses a solid-state spectrophotometer for non-invasive blood analyte detection that employs a plurality of Light Emitting Diodes (LED(s)) that emit at distinct, but overlapping, wavelengths in order to generate a continuous broad radiation spectrum and a linear detector array. It therefore differs from the present invention in that it uses an array of LEDs and an array of detectors.

Accordingly, a need exists for a system for the non-invasive sensing of glucose in a human subject that utilizes a pulsable and selectable wavelength, a selectable intensity monochromatic laser radiation source, involves a spectroscopic referencing scheme that does not require mechanical moving parts, and provides an improved instrument baseline stability by utilizing a dual-beam-double-reference spectrophotometer.

SUMMARY OF THE INVENTION

The present invention is directed to an apparatus for a non-invasive sensing of biological analytes in a sample. The apparatus includes an optics system having at least one radiation source and at least one radiation detector; a measurement system operatively coupled to the optics system; a control/processing system operatively coupled to the measurement system and an embedded software system; a user interface/peripheral system operatively coupled to the control/processing system for providing user interaction with the control/processing system; and a power supply system operatively coupled to the measurement system, the control/processing system, the user interface/peripheral system or any combination thereof for providing power to each of the systems. The embedded software system of the control/processing system processes signals obtained from the measurement system to determine a concentration of the biological analytes in the sample.

An absorbance spectrum obtained from the optics system may be used, together with a previously stored calibration vector, by the control/processing system to determine the concentration of the biological analytes in the sample. The sample may be one of interstitial fluid (ISF) of living tissue, the capillary bed of living tissue and/or a blood sample. The radiation source may be one of a selectable emission wavelength and selectable emission intensity, Transversely Pumped, Counter Propagating, Optical Parametric Oscillator (TPCOPO) device or a selectable emission wavelength and selectable emission intensity laser diode array. The radiation detector may be fabricated of InGaAs or Ge.

The biological analyte may be glucose, lipids or alcohol. An emission spectrum of the radiation source may cover a range of about 1,200 nm to about 1,900 nm and a responsivity of the radiation detector may cover a range of about 1,200 nm to about 1,900 nm, if the biological analyte is glucose or lipids. An emission spectrum of the radiation source may cover a range of about 800 nm to about 1,300 nm and a responsivity of the radiation detector may cover a range of about 800 nm to about 1,300 nm, if the biological analyte is alcohol.

The user interface/peripheral system may be configured to alert a user, in case of pending hypoglycemia or hyperglycemia, by an audible tone and/or the display of a text message; alert other individuals equipped with a Bluetooth alarm, in case of pending hypoglycemia, using a Bluetooth module; determine the user's location using a Global Positioning System module and, in case of hypoglycemia, transmit an emergency text message to a telephone number or relay biological analyte concentration data to a centralized server; and relay coded glucose concentration readings when they are taken to an insulin pump programmed to recognize the code and be in connection with the user, via the Bluetooth module for the purpose of automatic release of insulin.

The at least one radiation source may be fabricated from optical crystals, semiconductor material monolayer structures or any combination thereof. A semiconductor pump source may be integrated with a beam steering structure and a TPCOPO layer to achieve emission wavelength selection and intensity. In one embodiment, the at least one radiation source includes a pair of GaAs Bragg reflectors with a GaAs TPCOPO active layer, a GaAs narrowband coherent source pump and GaAs Electro-Optical beam deflecting layer. The pump source and beam steering structure may be parallel to the TPCOPO layer along the entire length of a Bragg cavity or reside at one end of the Bragg cavity to allow for beam steering before launching the pump source into the Bragg cavity containing the TPCOPO layer. Separate electrical connection means may be made to the pump layer and the GaAs Electro-Optical beam deflecting layer. An applied electric current to the pump layer may determine an intensity of emitted radiation, and an applied voltage to the GaAs Electro-Optical beam deflecting layer may determine a wavelength of emitted radiation.

The present invention is also directed to a method for the non-invasive sensing of biological analytes in a sample through spectrophotometric referencing utilizing two beams, each close in space (hereinafter referred to as "TECS") applicable to measuring interstitial fluid diffuse reflectance. The method includes the steps of: providing an optics system utilizing a first radiation source and a second radiation source and a first radiation detector and a second radiation detector, thereby establishing four optical beam paths close in space through the system; modulating the sources with different time functions; configuring the optics system in a manner in which all optical elements of the optics system transmit and/or reflect the beams; separating a first pair of the beams and a second pair of the beams at one point in the system, focusing the first pair of beams on a user's skin and focusing the second pair of beams into a reference sample; demodulating signals produced by the first detector and the second detector and separating signals due to the beams; and computing a spectrophotometric transmittance as a ratio of a first ratio to a second ratio.

The first ratio may be the ratio of a skin diffuse reflectance signal incident on the second radiation detector due to radiation from the first radiation source to a reference diffuse reflectance signal incident on the second radiation detector due to radiation of the second radiation source, and the second ratio may be an instrument signal incident on the first radiation detector due to radiation of the first radiation source to an instrument signal incident on the first radiation detector due to radiation of the second radiation source. The spectrophotometric transmittance may be used to determine a concentration of biological analytes in the sample. The optics system may have an area of separation between a sample beam and a reference beam that is restricted to an interior portion of an optical glass element. The area of separation between the sample beam and the reference beam may be protected by an enclosure.

These and other features and characteristics of the present invention, as well as the methods of operation and functions of the related elements of structures, will become more apparent upon consideration of the following description and the appended claims with reference to the accompanying drawings, all of which form a part of this specification, wherein like reference numerals designate corresponding parts in the various figures. As used in the specification and the claims, the singular form of "a", "an", and "the" include plural referents unless the context clearly dictates otherwise.

DETAILED DESCRIPTION OF THE PRESENT INVENTION

For purposes of the description hereinafter, the terms "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Figure 1:
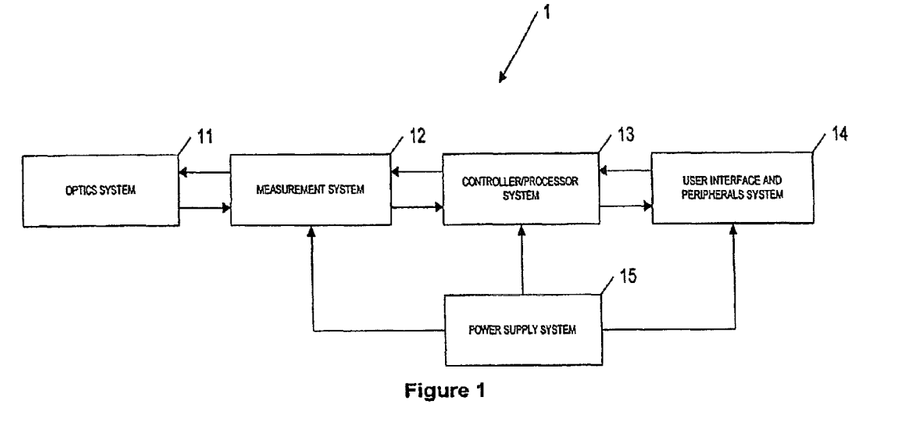
FIG. 1 is a schematic view of an apparatus for the sensing of biological analytes in a sample in accordance with the present invention.

With reference to FIG. 1, an apparatus 1 for the determination of biological analytes includes an Optics System 11, a Measurement System 12, a Controller/Processor System 13, a User Interface/Peripheral System 14, a Power Supply System 15, and an embedded software system (not shown). Each system contains several sub-systems.

Figure 2:
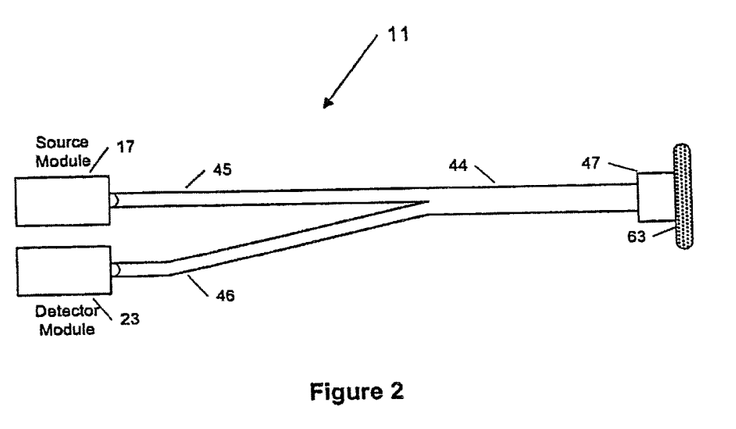
FIG. 2 is a schematic view of the optics system of the apparatus of FIG. 1.

With reference to FIG. 2 and with continuing reference to FIG. 1, Optic System 11 includes a radiation source module 17, a radiation detection module 23 and a fiber optics probe 44 operatively coupled to the source module 17, the detector module 23 and skin 63 of a user via contact through a special attachment 47. Fiber optics probe 44 includes several fibers 45 bundled together to transfer radiation from the source module 17 to skin 63 and several other fibers 46 are bundled together to pick up the diffuse reflectance from skin 63 and transfer it to the detector module 23. Source module 17 may be, but is not limited to, one or more TPCOPOs or a laser diode array. The source emission spectrum covers the wavelength range of 1,200 nm to 1,900 nm for glucose and lipids detection and 800 nm to 1,300 nm for alcohol detection, emitting at 64 to 256 distinct wavelengths. The detector is responsive equivalently over the same range. Detector module 23 may be, but is not limited to, a Ge detector, an InGaAs detector, or an extended InGaAs detector.

Figure 3:
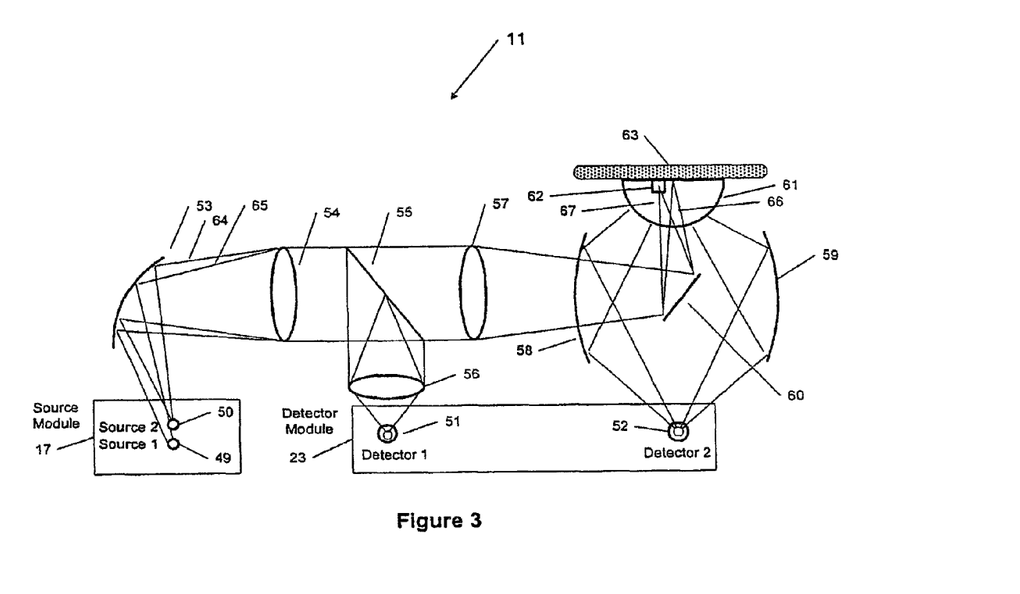
FIG. 3 is a schematic diagram of an additional embodiment of the optics system of the apparatus of FIG. 1.

With reference to FIG. 3 and with continuing reference to FIG. 1, an alternate embodiment of the Optics System 11 includes at least two radiation sources, Source "1" 49 and Source "2" 50 and at least two radiation detectors, Detector "1" 51 and Detector "2" 52.

Source "1" 49 and Source "2" 50 may be, but are not limited to, one or more TPCOPOs or a laser diode array. Desirably, Source "1" 49 and Source "2" 50 are pulsable and selectable wavelength and selectable intensity monochromatic laser radiation sources. The use of a selectable emission wavelength solid-state radiation source lends to using a single photodetector and no need for a spectrograph, and therefore has the advantages of small size, battery operation, wearability, improved stability and improved drift. In addition, use of a source that is capable of being switched on/off very rapidly and of emitting at one wavelength at a time, allows higher radiation power, resulting in increased diffuse reflectance signal and signal-to-noise ratio due to ISF, but especially due to capillary blood that is detectable and therefore enabling probing of the capillary blood glucose in addition to ISF glucose. As discussed above, such a radiation source may be a TPCOPO, a laser diode array or others. The laser diode array provides radiation at several wavelengths covering the required broad spectrum. While the TPCOPO uses only one laser diode as a pump, the laser diode array uses one laser diode for each wavelength. A broad spectral coverage source finds applications beyond spectroscopy wherever monochromatic light sources have applications such as telecommunications, displays, room lighting, etc. Compact, high efficiency, rapidly and widely tunable solid-state monochromatic light sources are applicable in all of these fields; however, individually, existing technologies such as monochromators, optical parametric oscillators (OPO), light emitting diodes (LED), laser diodes tuned via thermal, piezoelectric or electro-optic action, and dye lasers have some but not all of the above features.

Detector "1" 51 and Detector "2" 52 may be, but are not limited to, Ge detectors, InGaAs detectors, or extended InGaAs detectors. The two radiation sources and the two radiation detectors have identical spectral coverage over 1,200 nm to 1,900 nm for glucose and lipids detection and 800 nm to 1,300 nm for alcohol detection. The sources emit M (64-256) distinct wavelengths and the detectors are responsive equivalently over the same range.

A first mirror 53 and a first lens 54 direct two beams 64 and 65 from the two sources onto a beam splitter 55 where a small portion of the radiation power is reflected and is directed through a second lens 56 to Detector "1" 51. Second lens 56 may be, but is not limited to, a Kohler lens that images the aperture of beam splitter 55 onto Detector "1" 51. Most of the optical power, however, is transmitted through the beam splitter 55, a third lens 57 and a second mirror 60 to an immersion lens 61 that is in contact with the user's skin 63. The beam 65 of Source "2" 50 is focused onto a reference standard 62, such as spectralon, which is immersed and protected in immersion lens 61, while the beam 64 of Source "1" 49 is focused on the skin 63. Immersion lens 61 is dimensioned to a size large enough to allow significant separation of the skin beam and the reference beam to occur only within the glass of immersion lens 61. Immersion lens 61 is constructed from, for example, Bk-7, fused silica, or sapphire. Both beams are collected by pick-up optics 58 and 59 and concentrated onto Detector "2" 52.

Detector "2" 52 is used to detect both the skin and reference signal that form the biological beam pair, whereas Detector "1" 51 is used to detect instrument stability beams such as an instrument beam pair. Defining signals resulting from the optical paths of the two beam pairs of incident radiation on the detectors as: $S_{11}$ instrument signal incident on Detector "1" 51 due to radiation of Source "1" 49, $S_{12}$ instrument signal incident on Detector "1" 51 due to radiation of Source "2" 50, $S_{21}$ skin diffuse reflectance signal incident on Detector "2" 52 due to radiation of Source "1" 49, and $S_{22}$ reference diffuse reflectance signal incident on Detector "2" 52 due to radiation of Source "2" 50. The transmission spectrum is computed as a ratio of two ratios:

$$T=(S_{21}/S_{22})/(S_{11}/S_{12}) \tag{Equation 1}$$

At any given time, during measurement, only one source is activated. If the two beam pairs are very close in space, they encounter identical transmissions, reflections, and disturbances and the effects of optical/electro-optical component drifts and disturbances are canceled out. Therefore, the expense of using two radiation sources provides sampling of the reference standard diffuse reflectance without having to move mirrors while, in addition, the use of two detectors provides instrument stability. Accordingly, this spectroscopic referencing scheme, TECS, does not require mechanical moving parts and provides improved instrument baseline stability by utilizing a dual-beam-double-reference spectrophotometer. This scheme utilizes two sources and two detectors, as described above, that form two beam pairs each sampled close in space that experience the same disturbances.

Figure 4:
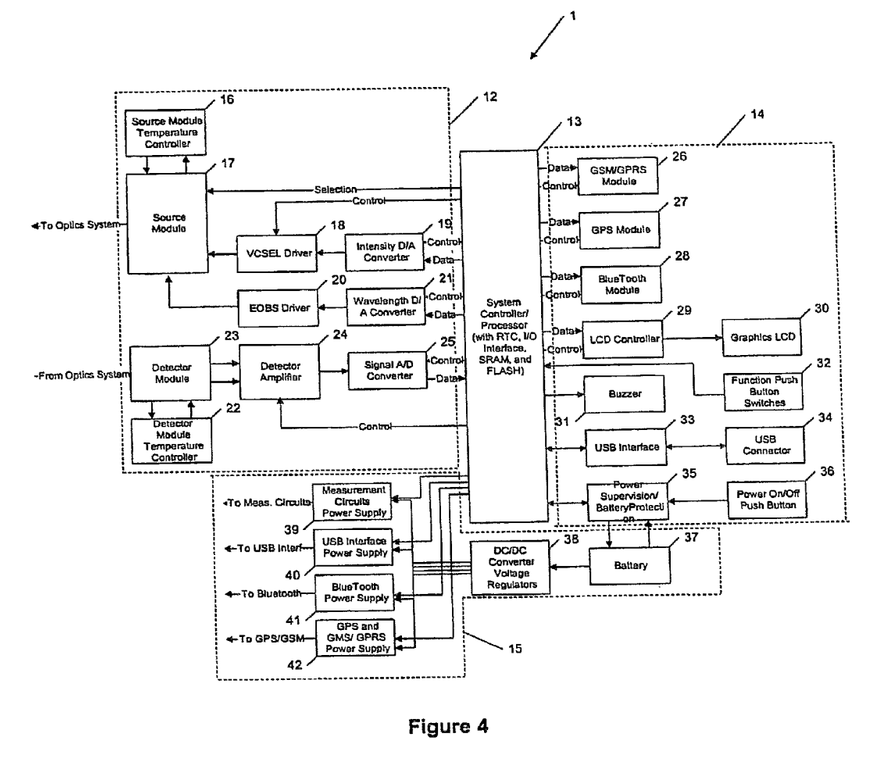
FIG. 4 is a detailed schematic view of the apparatus of FIG. 1.

With reference to FIG. 4, and continued reference to FIG. 1, a more detailed schematic diagram of one preferred embodiment of the apparatus 1 of the present invention is shown. The centralized control component of the apparatus 1 is the Controller/Processor System 13. Controller/Processor System 13 boots from a resident FLASH memory (non-volatile) that holds the program and executes the program from resident SRAM (Static Random Access Memory) and controls the Measurement System 12. Controller/Processor System 13, in conjunction with User Interface/Peripheral System 14, performs a variety of functions including, but not limited to, temporarily saves all diffuse reflectance and dark signals in SRAM, processes the signals to develop the absorbance spectrum, and subsequently determines glucose concentration, saves the data in FLASH memory, drives a buzzer 31, displays the data on a small size (1.5"×1.0") monochrome or color graphics LCD 30 via the LCD Controller 29, accepts input from the user via Function Push Button Switches 32, uploads data to a computer via the USB Interface 33 and USB Connector 34 or the BlueTooth Module 28, provides short distance remote alerts via the BlueTooth module 28, and determines user location via the GPS module 27 and provides long distance alerts via the GSM/GPRS module 26. Another push button switch, Power On/Off Push Button 36 serves for turning the apparatus 1 on. Pressing the same switch 36 will turn the apparatus off, but only after invocation by the Controller/Processor System 13 via the display 30 and subsequent confirmation by the user via the Function Push Button Switches 32. Controller/Processor System 13 also contains a Real Time Clock (RTC) (not shown) that keeps track of time even when the apparatus 1 is powered off and provides stamps of date and time to each measurement.

Controller/Processor System 13, in conjunction with User Interface/Peripheral System 14, is thereby provided with the ability to perform a variety of functions. For instance, Controller/Processor System 13 can display the last glucose reading and the time it was taken on LCD 30 as well as calculate and display the trend and rate. It can calculate and display on LCD 30 various statistics, such as moving average (trend) and daily moving min-max deviation over a selected time period and plot them versus time on LCD 30 when requested. It can provide the option to the user for selecting the units of glucose concentration mg/dL or mmol/L and can store up to a year-long set of glucose readings in nonvolatile memory together with time stamps reflecting the time they were taken, display, or upload to a computer when requested via USB interface 33 or Bluetooth module 28 as selected.

In cases of pending hypoglycemia or hyperglycemia, it can alert the user by an audible tone created by buzzer 31 and display a text message on LCD 30. Further, in cases of pending hypoglycemia, apparatus 1 can alert other individuals equipped with a Bluetooth alarm and located at a distance of up to 10 meters away using built Bluetooth module 28. Apparatus 1 can also determine the user's location through the use of GPS module 27 and, in case of hypoglycemia, can transmit an emergency text message to a telephone, such as emergency services "911" and/or any other preprogrammed telephone number, including a centralized sever by built in General Packet Radio Service (GPRS) or Global System for Mobile Communication (GSM) or simply relay glucose concentration data to centralized server for the purpose of telemedicine. Apparatus 1 may also relay glucose concentration readings at the time they are taken to an insulin pump, connected to the user, via Bluetooth module 28 and, together with the insulin pump, form an artificial pancreas. If apparatus 1 is used in such a manner, Controller/Processor System 13 must code the data by a pseudorandom sequence shared by both apparatus 1 and the insulin pump in order to avoid interference with other users who happen to be nearby.

With further reference to FIG. 4, Power Supply System 15 contains a rechargeable small size battery 37. Battery 37 may be, but is not limited to, a Li-Ion type battery. A Power Supervision/Battery Protection subsystem 35 protects battery 37 from over-discharge and short circuit conditions and notifies Controller/Processor System 13 when the battery voltage is low and must be recharged. It also contains DC/DC Converter Voltage Regulator sub-systems 39, 40, 41, and 42 that produce the necessary voltages for biasing all circuits and voltage distribution for various sub-systems with on/off capability under the control of Controller/Processor System 13.

Apparatus 1 may determine its status by self-testing Power Supply System 15 and Measurement System 12 prior to each measurement and warn the user in case of faults via buzzer 31 or LCD display 30. Apparatus 1 also monitors battery voltage and warns the user when replacement is necessary between glucose readings without interruption in monitoring, as battery charging will take place outside the unit to perpetuate continuous monitoring. Apparatus 1 also determines battery status by monitoring duration of service (how long the battery holds its charge in normal use) and warns the user when a new battery is necessary. Apparatus 1 may also automatically power down some circuitry between measurements in order to preserve battery life. Apparatus 1 also has the ability to request and obtain confirmation via User Interface/Peripheral System 14 to turn off apparatus 1 in response to Power On/Off Push Button 36 activation in order to avoid accidental power off.

Measurement System 12 includes the Radiation Source Module 17, a Source Module Temperature Controller 16, an EOBS Driver 20, a 16-bit Wavelength D/A Converter 21, a VCSEL Driver 18 and a 16-bit Intensity D/A Converter 19. It also includes Radiation Detection Module 23, a Detector Module Temperature Controller 22, a Detector Amplifier 24, and a Signal A/D Converter 25.

Figure 5:
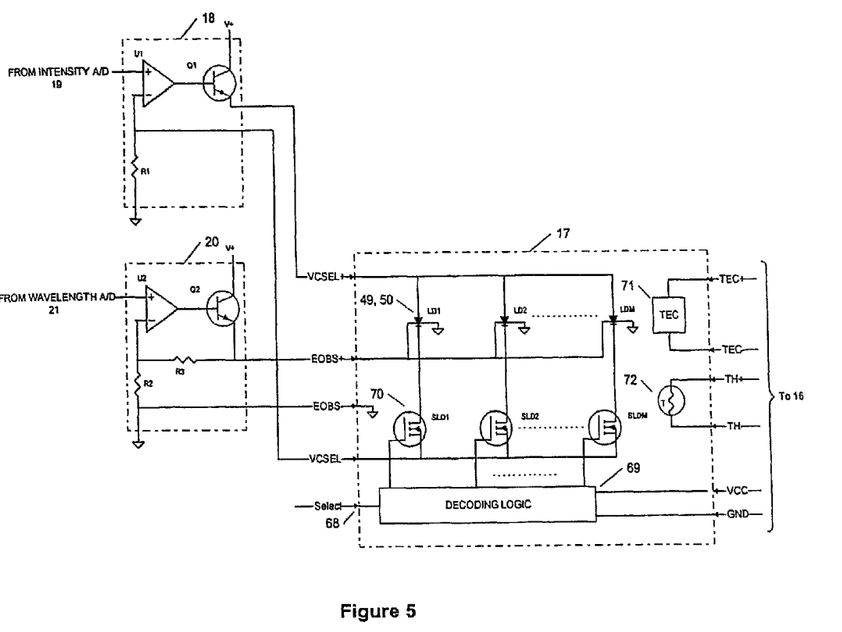
FIG. 5 is a schematic diagram of a radiation source module in accordance with the present invention.

With reference to FIG. 5 and with continuing reference to FIGS. 1 and 4, the circuit of Radiation Source Module 17, along with the circuits of EOBS Driver 20 and VCSEL Driver 18 are shown. Source "1" 49 or Source "2" 50 (LD1-LDM) has a radiation intensity that is selectable up to 500 mW by the voltage level of the Intensity D/A converter 19 via VCSEL Driver 18 and is switchable on/off by switching transistors SLD1-SLDM 70 for a short period (1-100 μs) under command by Controller/Processor System 13 over a Select control 68 and a Decoder 69. The source emission wavelength is also selectable by the voltage level of Intensity D/A converter 21 via EOBS Driver 20 over the mentioned range and mentioned distinct wavelengths. Radiation Source Module 17 also contains a thermoelectric cooler 71 (TEC) and an associated thermistor 72 to enable temperature control by Source Module Temperature Controller 16 at 25° C.

Figure 6:
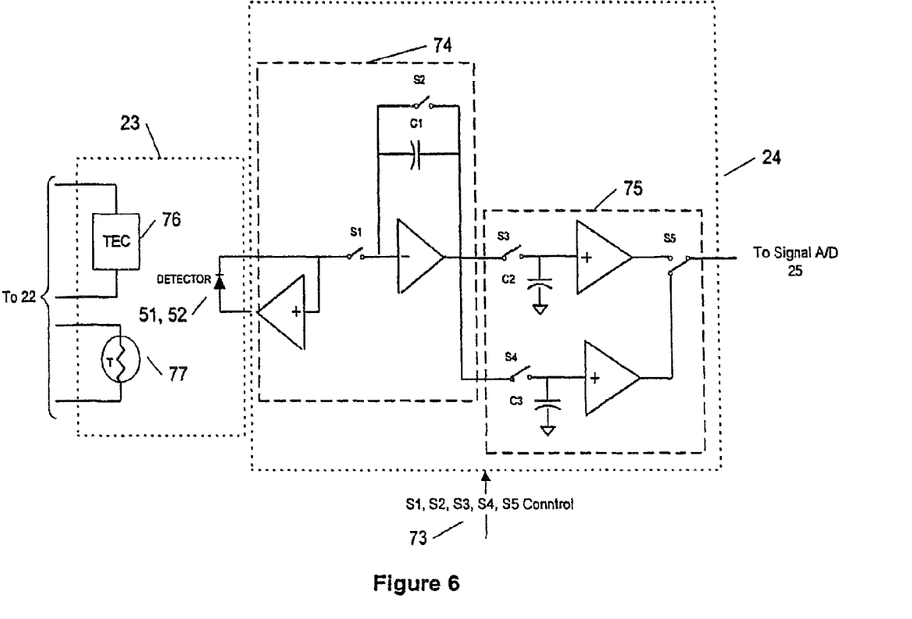
FIG. 6 is a schematic diagram of a radiation detection module in accordance with the present invention.

With reference to FIG. 6 and with continuing reference to FIGS. 1 and 4, the circuit of Radiation Detector Module 23, along with the circuit of the Detector Amplifier 24, is shown. Radiation Detector Module 23 includes one or two detectors 51, 52 that convert the optical diffuse reflectance signals to electrical signals and a TEC 76 and an associated thermistor 77 to enable temperature control of the detectors by Detector Module Temperature Controller 22 at 10° C. Detector Amplifier 24 process the electrical diffuse reflectance signal by a switched integrator circuit 74 and correlated double sampling circuit 75 under switch control by Controller/Processor System 13 and in synchronicity with switch control of the radiation. A 24-bit Signal A/D Converter 25 digitizes the reflectance signal and outputs it to Controller/Processor System 13. The acquisition of one full set of data, including skin, reference, and dark signals over all wavelength channels, takes 1-20 ms. Within a measurement time of approximately 10 seconds acquisition is repeated N times (500-10,000). The measurement, in continuous mode, can be repeated every 5 minutes with battery replacements every 12 hours or every 10 minutes with battery replacements every 24 hours.

The software of Controller/Processor System 13 processes the signals to minimize noise first, then computes transmittance and the absorbance spectra, and finally computes analyte concentrations. Theoretically, transmittance is defined as the ratio:

$$T = I/I_o = e^{-kd} \text{(Beer-Lambert law)} \quad \text{(Equation 2)}$$

I denotes the intensity of the diffuse reflectance in response to incident radiation of intensity $I_o$, k denotes the extinction coefficient (tissue or reference standard), and d denotes the penetration distance. In the case of ISF, the skin diffuse reflectance, the reference diffuse reflectance, and the photodetector dark current are measured. In the following description, bold letters denote vectors. The transmittance spectrum is computed as a double ratio $I_{skin}/I_o$ divided by $I_{ref}/I_o$. Therefore, $T = I_{skin}/I_{ref}$, hence bypassing the need to measure incident radiation, $I_o$. The detected radiation, $R_{skin}$, $R_{ref}$ includes a strong component $D_2$ due to detector dark current, which must be subtracted, plus uncorrelated noise. Therefore, after mean centering all signals the transmittance spectrum is computed as $T = (R_{skin} - D_2)/(R_{ref} - D_2)$ and the absorbance spectrum is by definition:

$$X = -\log T \quad \text{(Equation 3)}$$

The software sorts the sampled signals of skin, reference, and dark time sequences in a 3×N×M array. Each signal sequence skin, reference, and dark is low-pass filtered at 0.5 Hz by a sharp zero-phase digital filter to reduce excessive noise. To develop the ISF absorbance spectrum, the transmittance spectra are calculated first for each set of acquired data, then averaged, and absorbance is computed using the average transmittance spectrum. The development of the capillary absorbance spectrum, however, requires more processing. The skin diffuse reflectance signal, at each wavelength channel, contains a large DC part, due mostly to ISF diffuse reflectance with a small part due to capillary diffuse reflectance (~1%), a small part due to detector dark signal and a large portion due to uncorrelated white noise. This signal is modulated by heart pumping action with hill excursions occurring at the systolic phase of the heart and low excursions occurring at the diastolic phase. Accordingly, apparatus 1 provides for the measurement of glucose in the capillary vessels by utilizing a spectroscopic referencing scheme that does not require a reference standard and/or mechanical moving parts. Apparatus 1 thereby offers improved instrument baseline stability and processing that involves optimized synchronous detection of the time signal at each wavelength of the extremely small and slowly varying heart pulse modulated diffuse reflectance signal and forming the transmittance as a ratio of the maxima to the minima This referencing scheme samples one path that changes minutely close in time at the minimum and maximum photon path changes during each heart pulse.

Figure 7:
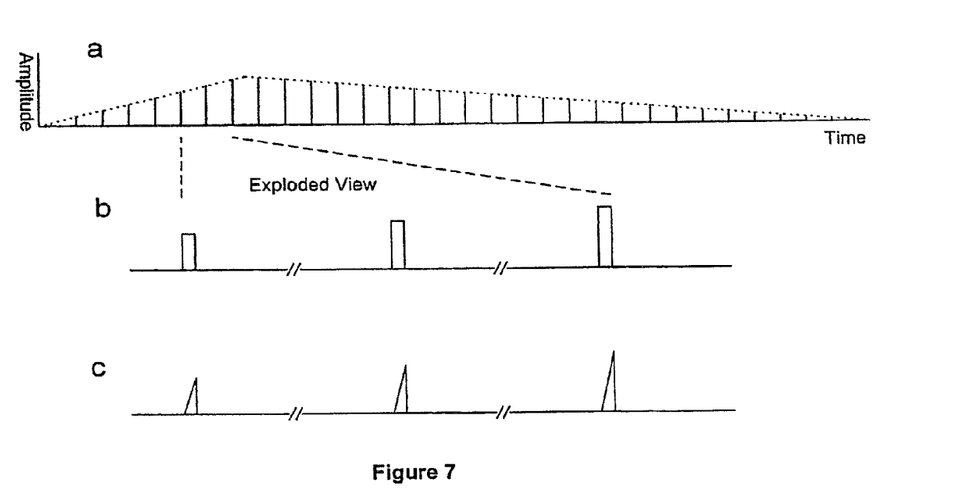
FIGS. 7a-7c are graphs illustrating one period of a discrete-time capillary diffuse reflectance signal at the output of the detector, an exploded view thereof and at the output of a switched integrator, respectively.

With reference to FIGS. 7a-7c, a single cycle of this signal at one wavelength channel, at the output of the detector, is shown. The signal is discrete in time because of the switching of the radiation source on for 1-100 μs and off for 1-20 ms between wavelength channels. The frequency spectrum of this signal contains one set of components at DC plus components at a heart rate as mentioned above and more sets of these signals at fundamental and harmonic frequencies of the switching signal. To apply Pulse Differential Spectroscopy (PDS), the excursions must be determined. Operating around DC this is accomplished as follows. Both signal sequences skin and dark are low-pass filtered at 2 Hz by a sharp zero-phase digital filter to reduce excessive noise. They are then high-pass filtered at 0.5 Hz by a sharp zero-phase digital filter to eliminate the strong DC component. The excursions can then be determined via FFT or by demodulation with a synchronous replica of the heart pulse signal.

A replica of the heart pulse signal can be developed by estimation of pulse rate using the time sequence of the skin diffuse reflectance signal at a channel with a wavelength around 1275 nm. Radiation at this wavelength penetrates the epidermis and reaches the capillary bed much deeper than any other wavelength. The transmittance is computed as mentioned above by averaging the peak positive excursions to/from $R_{skin}$ and averaging the peak negative excursions to/from $R_{ref}$ since there are 6-12 cycles over the measurement period. Alternatively, the excursions can be determined similarly by operating at the fundamental of the switching frequency. However, this method requires, in addition, down-conversion to DC by multiplication of the signals by a synchronous replica of the switching signal.

Finally the absorbance spectrum is used together with a previously stored calibration vector b, to predict glucose concentration:

$$y_P = X b \quad \text{(Equation 4)}$$

The calibration vector is obtained by Partial List Squares as:

$$b = (X^T X)^{-1} X^T y_R \quad \text{(Equation 5)}$$

$y_R$ are reference readings obtained with an accurate invasive device. The number of required acquired spectra and invasive reference readings for the purpose of calibration can be reduced drastically by adding a priori knowledge about the spectra in determining the calibration vector as discussed in the article entitled "On Wiener filtering and the physics behind statistical modeling" by Marbach. Accordingly, the required individual calibration time may be reduced from many days to a few hours.

With reference to FIGS. 8a-8c, the TPCOPO provides the means of obtaining optical parametric oscillation, and similar to a conventional OPO, the TPCOPO requires a pump. Tuning is achieved by changing the angle of incidence of the pump beam. The TPCOPO can be fabricated from conventional non-linear optical crystals such as, but not limited to, LiNbO3, KTP and others. However, the transverse design nature of the TPCOPO also allows for fabrication from semiconductor materials such as GaAs and ZnSe monolayer structures. By integrating a VCSEL semiconductor pump source and an electro-optic beam steering structure (EOBS) with a TPCOPO, all of the previously mentioned characteristics of a tunable light source are achieved. For instance, the device may be comprised of a pair of GaAs Bragg reflectors with the GaAs TPCOPO active layer, a GaAs solid state narrowband coherent source serving as a pump such as a VCSEL or others and a GaAs electro-optical beam-deflecting layer between them.

Figure 8:
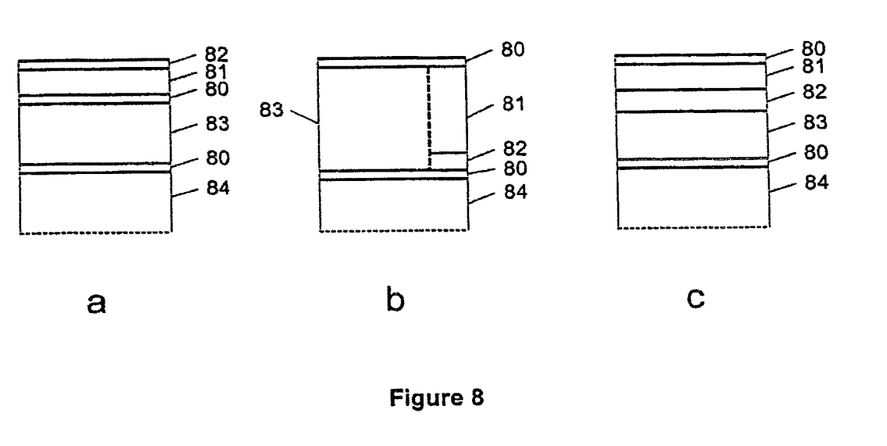
FIGS. 8a-8c are block diagrams of a transversely pumped counter propagating optical parametric oscillator in accordance with the present invention.

The TPCOPO layer and Bragg reflectors are designed for the wavelength of the pump. In this embodiment, the pump and beam steering elements can be either parallel to the TPCOPO layer along the entire length of the Bragg cavity or they can reside at one end of the Bragg cavity to allow for ample beam steering capacity before launching the pump into the Bragg cavity containing the TPCOPO layer. Electrical connections for the means of applying drive voltages are made to the pump and EOBS layers separately. Electrical power to the pump determines the optical output power and the electrical voltage applied to the EOBS layer determines the optical output energy (i.e., frequency). The described structure can be made either as a single element emitter or as an array. The structural layers of the TPCOPO shown in FIG. 8 are Bragg reflector 80, EOBS beam steering layer 81, pump 82, TPCOPO active layer 83, Device substrate 84. In FIG. 8a, the pump is located outside the Bragg cavity. This may be useful if the desired pump is not compatible with the EOBS or TPCOPO materials, the EOBS layer requires excessive path length for adequate beam steering or if the pump and or EOBS layers excessively absorb the pump or TPCOPO output frequencies. In this configuration, the EOBS layer can be substituted with an acousto-optic or piezo-electric beam steering layer and need not be "grown" onto the Bragg cavity. In FIG. 8b, the pump and EOBS layers are placed inside the Bragg cavity for higher conversion efficiency of the pump energy to output energy, but allow freedom of design for EOBS path length in the event the FOBS layer requires multiple passes of the pump wave for adequate angular deflection before entering the TPCOPO layer. In FIG. 8c, the pump, EOBS and TPCOPO layers are stacked on top of each other. This is the simplest design assuming the EOBS layer effectively deflects the pump output and neither the pump nor the EOBS layer excessively absorb either the pump or the output frequencies.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A method of spectrophotometric referencing that utilizes pulse differential spectroscopy applicable to capillary blood diffuse reflectance by:
   a) providing an optics system with at least one optical path which emits a plurality of narrow band pulses of near infrared light within a range of from about 1,200 nm to about 1,900 nm, each narrow band having a unique center emission wavelength, and each narrow band activated individually and sequentially during each scan cycle, said scan cycle occurring multiple times per second and continuously for a period equivalent to at least more than one cardiac cycle;
   b) repeatedly sampling at least multiple times per second, irrespective of the systolic and diastolic phases of the cardiac cycle, at each unique emission center wavelength within each of the plurality of the narrow bands within the wavelength range at least one path of the optics system through an external, diffusely-reflecting, capillary-bearing sample, wherein the optical path is time-varying as a result of heart pulsation and changes minutely close in time as a minimum and a maximum photon path changes during a heart pulse;
   c) synchronously detecting at each unique center emission wavelength of each narrow band, with each cycle of sequentially activating the plurality of narrow bands, a time-dependent diffuse reflectance signal of the optical path through the sample;
   d) computing a spectrophotometric absorbance at each unique center wavelength, as a ratio of a maxima to a minima of the time-dependent diffuse reflectance signal; and
   e) determining a concentration of biological analytes in a sample using the spectrophotometric absorbance.

2. The method of claim 1, further comprising the step of synchronizing a detected time signal at each unique center emission wavelength of each narrow band for each scan cycle.

3. The method of claim 1, further comprising the steps of:
   (i) providing a radiation source having a plurality of narrow band emitters for sequentially emitting a plurality of emission bands over a selected wavelength range in the near infrared, each emission band having the unique center emission wavelength and each emission band activated individually with each scan cycle repeated multiple times per second continuously for a period equivalent to at least two cardiac cycles;
   (ii) obtaining a spectral measurement taken during each scan cycle at the unique center emission wavelength of a specified narrow band emitter;
   (iii) calculating a ratio between the spectral measurements taken at the time dependent scan cycle of the minimum reflectance and the spectral measurement taken at the time dependent scan cycle of the maximum reflectance, for each unique center wavelength of each narrow band thereby providing a sensed signal of the biological analyte.

4. The method of claim 3, wherein steps (ii)-(iv) are repeated for a subsequent, specified narrow band emitter.

5. The method of claim 3, wherein the spectral measurement taken at a diastolic state provides a signal including a bulk skin signal and a base capillary signal, and the spectral measurement taken at a systolic state provides a signal including a bulk skin signal, a base capillary signal and a perturbed capillary signal.

6. The method of claim 5, further comprising the steps of:
calculating the perturbed capillary signal using the calculated ratio of step (iii); and
associating the perturbed capillary signal with the specified biological analyte.

7. The method of claim 3, wherein the specified narrow band emitter is activated at least 100 times per second.

8. The method of claim 3, wherein the radiation source is a laser diode array, an edge-emitting laser diode array, a surface-emitting laser diode array, a semiconductor laser diode array, an alternate laser diode array or any combination thereof.

9. The method of claim 3, wherein the radiation source is a laser diode array having a plurality of discrete laser diode elements.

10. The method of claim 9, wherein each discrete laser diode element has a unique center emission wavelength, and the center emission wavelengths of the plurality of laser diode elements are spaced between about 1,200 nm and about 1,900 nm.

11. The method of claim 9, wherein each discrete laser diode element is individually addressable and configured to be activated according to a sequence.

\* \* \* \* \*